(12) United States Patent
Uesugi et al.

(10) Patent No.: US 8,853,273 B2
(45) Date of Patent: Oct. 7, 2014

(54) MEDICINAL AGENT FOR PREVENTION AND/OR TREATMENT OF HEPATOCELLULAR CARCINOMA

(75) Inventors: Ken Uesugi, Musashino (JP); Tetsuro Sano, Saitama (JP); Takatoshi Ozawa, Kawasaki (JP); Kazuhide Shimada, Kitamoto (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 13/811,927

(22) PCT Filed: Aug. 10, 2011

(86) PCT No.: PCT/JP2011/068226
§ 371 (c)(1),
(2), (4) Date: Jan. 24, 2013

(87) PCT Pub. No.: WO2012/020785
PCT Pub. Date: Feb. 16, 2012

(65) Prior Publication Data
US 2013/0123363 A1 May 16, 2013

(30) Foreign Application Priority Data
Aug. 11, 2010 (JP) .................... 2010-180071

(51) Int. Cl.
*A61K 31/202* (2006.01)
*A61K 31/198* (2006.01)
*A61K 31/203* (2006.01)

(52) U.S. Cl.
CPC ........... *A61K 31/202* (2013.01); *A61K 31/203* (2013.01); *A61K 31/198* (2013.01)
USPC ...................................................... 514/560

(58) Field of Classification Search
USPC ............................................. 514/560, 561
See application file for complete search history.

(56) References Cited

U.S. PATENT DOCUMENTS

2007/0197647 A1   8/2007   Kumada et al.

FOREIGN PATENT DOCUMENTS

| EP | 0 847 754 A1 | 6/1998 |
| EP | 1 582 207 A1 | 10/2005 |
| JP | 2006-241140 A | 9/2006 |
| WO | 2006 006729 | 1/2006 |

OTHER PUBLICATIONS

Medkoo (2013); 3 pages.*
Combined Chinese Office Action and Search Report issued on Nov. 5, 2013 in Chinese Patent Application No. 201180039060.9 (with partial English translation and with English translation of category of cited documents).
Junpei Iwasa, et al., "Dietary supplementation with branched-chain amino acids suppresses diethylnitrosamine-induced liver tumorigenesis in obese and diabetic C57BL/KsJ-db/db mice",Cancer Science, vol. 101, No. 2, Feb. 28, 2010, pp. 460-467.
Muto, Y., et al., "Prevention of Second Primary Tumors by an Acyclic Retinoid, Polyprenoic Acid, in Patients with Hepatocellular Carcinoma," The New England Journal of Medicine, vol. 334, No. 24, pp. 1561-1567, (Jun. 13, 1996).
Nakanishi, H., et al., "The Efficacy of Branched Chain Amino Acid for the Treatment of Liver Cirrhosis," Gastroenterology, vol. 49, No. 2, pp. 208-212, (Aug. 28, 2009) (with English translation).
Tsuchiya, K., et al., "Oral Supplementation with Branched-Chain Amino Acids Improves Survival and Recurrence-free Survival After Successful Treatment of Hepatocellular Carcinoma in Patients with Cirrhosis: A Prospective Study," Hepatology, vol. 46, No. 4, pp. 401A-402A, (Oct. 2007).
Suzuki, K., "Clinical Joint Research on the Inhibitory Effect of Branched-Chain Amino Acid Preparations on Recurrence of Hepatocellular Carcinoma after Treatment Thereof," Scientific Research of Ministry of Health, Labour and Welfare, Research Project of Urgent Countermeasures toward Overcoming Hapatitis and Similar Conditions, pp. 37-64, (Mar. 2010) (with Partial English Translation).
"Liver Cancer Study Group of Japan," Survey and Follow-up Study of Primary Liver Cancer in Japan-Report 18, Total 10 Pages (2009) (with Partial English Translation).
Nagasue, N., "Long-term oral administration of branched chain amino acids after curative resection of hepatocellular carcinoma: a prospective randomized trial," British Journal of Surgery, vol. 85, pp. 1525-1531, (1998).
International Search Report Issued Sep. 27, 2011 in PCT/JP11/68226 Filed Aug. 10, 2011.
Extended European Search Report issued on Jan. 7, 2014 in the corresponding European Patent Application No. 11816449.0.

* cited by examiner

*Primary Examiner* — Shirley V Gembeh
(74) *Attorney, Agent, or Firm* — Oblon, Spivak, McClelland, Maier & Neustadt, L.L.P.

(57) ABSTRACT

The present invention relates to provision of a pharmaceutical agent useful for the prevention and treatment of hepatocellular carcinoma, and the pharmaceutical agent for the prevention and/or treatment of hepatocellular carcinoma contains an acyclic retinoid, a salt thereof, or a solvate of any of these, in combination with a branched-chain amino acid, a salt thereof, or a solvate of any of these.

30 Claims, 1 Drawing Sheet

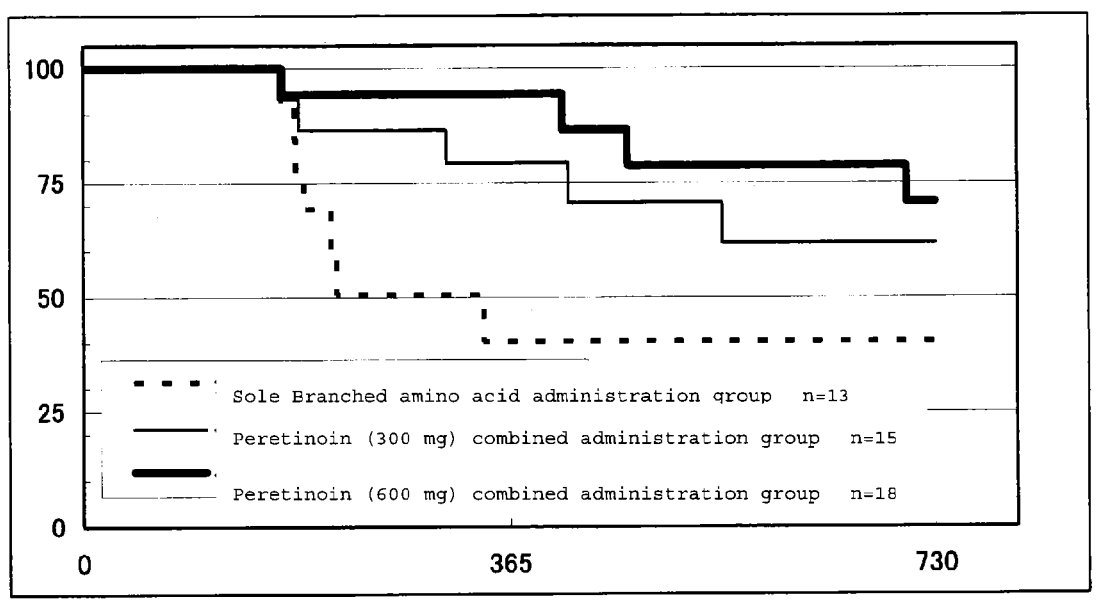

MEDICINAL AGENT FOR PREVENTION AND/OR TREATMENT OF HEPATOCELLULAR CARCINOMA

This application is a National Stage of PCT/JP11/068,226 filed Aug. 10, 2011 and claims the benefit of JP 2010-180071 filed Aug. 11, 2010.

TECHNICAL FIELD

The present invention relates to a pharmaceutical agent for the prevention and/or treatment of hepatocellular carcinoma.

BACKGROUND ART

In 2009, 344,000 people in Japan died from malignant neoplasm, which was the top cause of death. Among them, the number of deaths from hepatocellular carcinoma exceeded 30,000. The number of deaths by hepatocellular carcinoma has increased year by year and has almost tripled over the past 20 years.

Among the hepatocellular carcinoma cases in Japan, 90% or more have been reported to be persistent infection (chronic hepatitis) caused by hepatitis B virus (HBV, hereinafter may be referred to as HBV) and hepatitis C virus (HCV, hereinafter may be referred to as HCV). Thus, viral hepatitis is a key disease for the onset of hepatocellular carcinoma. Meanwhile, non-alcoholic steatohepatitis (hereinafter may be abbreviated to as "NASH") is a type of hepatitis triggered by accumulation of fat in the liver. Oxidative stress on fatty liver, insulin resistance, proinflammatory cytokine, etc., lead to transition from fatty liver or aggravation of pathological condition. In recent years, cases of the metabolic syndrome have increased, and there are concerns about an increase of the onset of NASH, and subsequent transition to liver fibrosis, cirrhosis, and hepatocellular carcinoma. Thus, NASH as well as viral hepatitis is a key disease involved in the onset of hepatocellular carcinoma.

Currently, hepatocellular carcinoma is treated through, for example, techniques including surgical therapies (e.g., hepatectomy and liver transplantation); local medical therapies including percutaneous ethanol injection therapy, radiofrequency ablation, and percutaneous microwave coagulation therapy; catheterization such as transcatheter arterial embolization or hepatic artery reservoir therapy; and chemotherapy such as therapy by use of a molecular target drug. However, even in a current stage when these therapies are available, hepatocellular carcinoma has recurred at high occurrence. Specifically, within 2 years from the time of diagnosis, intrahepatic recurrence (secondary carcinogenesis) is observed in 28.8% of hepatocellular carcinoma patients (Non-Patent Document 1), and repetition of recurrence results in death of many patients. Therefore, in addition to early-stage detection and treatment of hepatocellular carcinoma, inhibition of transition from chronic hepatitis to hepatocellular carcinoma, and inhibition of recurrence of hepatocellular carcinoma after treatment thereof are thought to become important issues, and a therapy positively inhibiting recurrence of hepatocellular carcinoma in the remaining liver after treatment thereof is conceivably very important. However, at present, there has been established no therapeutic method for inhibiting recurrence of hepatocellular carcinoma.

Meanwhile, one pharmaceutical agent employed in the chemotherapy of hepatocellular carcinoma is a molecular target drug, sorafenib (trade name: Nexavar (registered trademark)). This drug is employed only in systemic chemotherapy for non-resectable hepatocellular carcinoma, and various severe adverse side effects are reported therewith. In addition, there have not been established efficacy and safety of adjuvant chemotherapy following the surgical or local medicinal therapy for hepatocellular carcinoma. Therefore, there is keen demand for an effective and safe drug which can be used after the surgical or local medicinal therapy for hepatocellular carcinoma.

As another compound, (2E,4E,6E,10E)-3,7,11,15-tetramethylhexadeca-2,4,6,10,14-pentaenoic acid (hereinafter may be referred to as "peretinoin") has been proven to have a hepatocellular carcinoma recurrence inhibitory action, from the clinical study result that recurrence of hepatocellular carcinoma after radical treatment thereof was significantly inhibited through long-term administration of the compound for one year. In addition, peretinoin causes substantially no liver disorders and provides no substantial adverse side effects which other retinoids provide, thereby serving as a safety drug (Non-Patent Document 2).

Meanwhile, branched-chain amino acids are used for ameliorating encephalopathy concomitant with chronic liver disorders, for ameliorating hypoalbuminemia of decompensated cirrhosis patients, who suffer hypoalbuminemia even under sufficient diet conditions, and for ameliorating other conditions. There has also been reported that a drug containing three branched-chain amino acids, isoleucine, leucine, and valine, has an inhibitory action on the onset and progress of hepatocellular carcinoma in patients of cirrhosis triggered by HCV. However, the above-reported research was limited to male patients of ages 25 to 75, and no effects are reported with respect to female patients or male patients outside the range of age. In addition, the report fails to describe or suggest that these drugs are effective on inhibition of recurrence of hepatocellular carcinoma after radical treatment thereof (Patent Document 1). Furthermore, there is a report describing that the drug containing the branched-chain amino acids is not potent to inhibition in recurrence of hepatocellular carcinoma after radical treatment thereof, from the viewpoints of either cumulative cancer recurrence rate or survival rate (Non-Patent Document 3). Thus, it has been suggested that inhibition of recurrence of hepatocellular carcinoma after the treatment thereof is more difficult than inhibition of onset and progress of hepatocellular carcinoma.

PRIOR ART DOCUMENTS

Patent Documents

Patent Document 1: WO2006/006729

Non-Patent Documents

Non-Patent Document 1: 18th Follow-Up Survey Report of Primary Liver Cancer, Liver Cancer Study Group of Japan (2009)

Non-Patent Document 2: N. Eng. J. Med. 334(24), 1561-1567 (1996)

Non-Patent Document 3: Br. J. Surg. 84, 1525-1531 (1997)

SUMMARY OF THE INVENTION

Problems to be Solved by the Invention

The present invention relates to provision of a pharmaceutical agent useful for the prevention and/or treatment of hepatocellular carcinoma.

Means for Solving the Problem

The present inventors have conducted extensive studies in order to solve the aforementioned problem, and have found that use of an acyclic retinoid such as peretinoin, in combination with a branched-chain amino acid, results in a remarkable inhibitory effect on recurrence of hepatocellular carcinoma after the treatment thereof, whereby the combination of an acyclic retinoid and a branched-chain amino acid can serve as a useful pharmaceutical agent for the prevention and/or treatment of hepatocellular carcinoma. The present invention has been accomplished on the basis of this finding.

Specifically, the present invention provides a pharmaceutical agent for the prevention and/or treatment of hepatocellular carcinoma, the agent containing an acyclic retinoid, a salt thereof, or a solvate of any of these, in combination with a branched-chain amino acid, a salt thereof, or a solvate of any of these.

The present invention is directed to the following.

[1] A pharmaceutical agent for the prevention and/or treatment of hepatocellular carcinoma, the agent containing an acyclic retinoid, a salt thereof, or a solvate of any of these, in combination with a branched-chain amino acid, a salt thereof, or a solvate of any of these.

[2] The pharmaceutical agent as described in [1] above, wherein the acyclic retinoid is peretinoin.

[3] The pharmaceutical agent as described in [1] or [2] above, wherein the branched-chain amino acid includes a combination of isoleucine, leucine, and valine.

[4] The pharmaceutical agent as described in any one of [1] to [3] above, wherein the prevention and/or treatment of hepatocellular carcinoma is inhibition of recurrence of hepatocellular carcinoma after the treatment thereof.

[5] The pharmaceutical agent as described in any one of [1] to [4] above, wherein the hepatocellular carcinoma is caused by a hepatitis virus or non-alcoholic steatohepatitis.

[6] The pharmaceutical agent as described in [5] above, wherein the hepatitis virus is hepatitis C virus or hepatitis B virus.

[7] The pharmaceutical agent as described in any one of [1] to [6] above, which is in the form of a single preparation (combination drug) containing an acyclic retinoid, a salt thereof, or a solvate of any of these, in combination with a branched-chain amino acid, a salt thereof, or a solvate of any of these.

[8] The pharmaceutical agent as described in any one of [1] to [6] above, which is in the form of a kit preparation containing a preparation containing an acyclic retinoid, a salt thereof, or a solvate of any of these, in combination with a preparation containing a branched-chain amino acid, a salt thereof, or a solvate of any of these.

[9] A pharmaceutical agent containing an acyclic retinoid, a salt thereof, or a solvate of any of these, to be administered in combination with a branched-chain amino acid, a salt thereof, or a solvate of any of these, for the prevention and/or treatment of hepatocellular carcinoma.

[10] The pharmaceutical agent as described in [9] above, which is in the form of a kit containing the following (1) and (2):
 (1) a pharmaceutical agent for the prevention and/or treatment of hepatocellular carcinoma, the agent containing an acyclic retinoid, a salt thereof, or a solvate of any of these; and
 (2) a direction which directs the pharmaceutical agent to be administered in combination with a branched-chain amino acid, a salt thereof, or a solvate of any of these.

[11] A pharmaceutical agent containing a branched-chain amino acid, a salt thereof, or a solvate of any of these, to be administered in combination with an acyclic retinoid, a salt thereof, or a solvate of any of these, for the prevention and/or treatment of hepatocellular carcinoma.

[12] The pharmaceutical agent as described in [11] above, which is in the form of a kit containing the following (1) and (2):
 (1) a pharmaceutical agent for the prevention and/or treatment of hepatocellular carcinoma, the agent containing a branched-chain amino acid, a salt thereof, or a solvate of any of these; and
 (2) a direction which directs the pharmaceutical agent to be administered in combination with an acyclic retinoid, a salt thereof, or a solvate of any of these.

[13] The pharmaceutical agent as described in any one of [9] to [12] above, wherein the acyclic retinoid is peretinoin.

[14] The pharmaceutical agent as described in any one of [9] to [13] above, wherein the branched-chain amino acid includes a combination of isoleucine, leucine, and valine.

[15] The pharmaceutical agent as described in any one of [9] to [14] above, wherein the prevention and/or treatment of hepatocellular carcinoma is inhibition of recurrence of hepatocellular carcinoma after the treatment thereof.

[16] The pharmaceutical agent as described in any one of [9] to [15] above, wherein the hepatocellular carcinoma is caused by a hepatitis virus or non-alcoholic steatohepatitis.

[17] The pharmaceutical agent as described in [16] above, wherein the hepatitis virus is hepatitis C virus or hepatitis B virus.

[18] A method for preventing and/or treating hepatocellular carcinoma, the method including administering an effective amount of an acyclic retinoid, a salt thereof, or a solvate of any of these, and an effective amount of a branched-chain amino acid, a salt thereof, or a solvate of any of these, to a patient in need thereof, simultaneously or separately at different points in time.

[19] The method as described in [18] above, wherein the acyclic retinoid is peretinoin.

[20] The method as described in [18] or [19] above, wherein the branched-chain amino acid includes a combination of isoleucine, leucine, and valine.

[21] The method as described in any one of [18] to [20] above, wherein the prevention and/or treatment of hepatocellular carcinoma is inhibition of recurrence of hepatocellular carcinoma after the treatment thereof.

[22] The method as described in any one of [18] to [21] above, wherein the hepatocellular carcinoma is caused by a hepatitis virus or non-alcoholic steatohepatitis.

[23] The method as described in [22] above, wherein the hepatitis virus is hepatitis C virus or hepatitis B virus.

[24] Use of an acyclic retinoid, a salt thereof, or a solvate of any of these, in combination with a branched-chain amino acid, a salt thereof, or a solvate of any of these, for production of a pharmaceutical agent for the prevention and/or treatment of hepatocellular carcinoma.

[25] Use as described in [24] above, wherein the acyclic retinoid is peretinoin.

[26] Use as described in [24] or [25] above, wherein the branched-chain amino acid includes a combination of isoleucine, leucine, and valine.

[27] Use as described in any one of [24] to [26] above, wherein the prevention and/or treatment of hepatocellular carcinoma is inhibition of recurrence of hepatocellular carcinoma after the treatment thereof.

[28] Use as described in any one of [24] to [27] above, wherein the hepatocellular carcinoma is caused by a hepatitis virus or non-alcoholic steatohepatitis.

[29] Use as described in [28] above, wherein the hepatitis virus is hepatitis C virus or hepatitis B virus.

[30] An acyclic retinoid, a salt thereof, or a solvate of any of these, to be administered in combination with a branched-chain amino acid, a salt thereof, or a solvate of any of these, for the prevention and/or treatment of hepatocellular carcinoma.

[31] The acyclic retinoid, a salt thereof, or a solvate of any of these as described in [30] above, wherein the acyclic retinoid is peretinoin.

[32] The acyclic retinoid, a salt thereof, or a solvate of any of these as described in [30] or [31] above, wherein the branched-chain amino acid includes a combination of isoleucine, leucine, and valine.

[33] The acyclic retinoid, a salt thereof, or a solvate of any of these as described in any one of [30] to [32] above, wherein the prevention and/or treatment of hepatocellular carcinoma is inhibition of recurrence of hepatocellular carcinoma after the treatment thereof.

[34] The acyclic retinoid, a salt thereof, or a solvate of any of these as described in any one of [30] to [33] above, wherein the hepatocellular carcinoma is caused by a hepatitis virus or non-alcoholic steatohepatitis.

[35] The acyclic retinoid, a salt thereof, or a solvate of any of these as described in [34] above, wherein the hepatitis virus is hepatitis C virus or hepatitis B virus.

[36] A branched-chain amino acid, a salt thereof, or a solvate of any of these, to be administered in combination with an acyclic retinoid, a salt thereof, or a solvate of any of these, for the prevention and/or treatment of hepatocellular carcinoma.

[37] The branched-chain amino acid, a salt thereof, or a solvate of any of these as described in [36] above, wherein the acyclic retinoid is peretinoin.

[38] The branched-chain amino acid, a salt thereof, or a solvate of any of these as described in [36] or [37] above, wherein the branched-chain amino acid includes a combination of isoleucine, leucine, and valine.

[39] The branched-chain amino acid, a salt thereof, or a solvate of any of these as described in any one of [36] to [38] above, wherein the prevention and/or treatment of hepatocellular carcinoma is inhibition of recurrence of hepatocellular carcinoma after the treatment thereof.

[40] The branched-chain amino acid, a salt thereof, or a solvate of any of these as described in any one of [36] to [39] above, wherein the hepatocellular carcinoma is caused by a hepatitis virus or non-alcoholic steatohepatitis.

[41] The branched-chain amino acid, a salt thereof, or a solvate of any of these as described in [40] above, wherein the hepatitis virus is hepatitis C virus or hepatitis B virus.

Effects of the Invention

The present invention enables provision of an excellent pharmaceutical agent for the prevention and/or treatment of hepatocellular carcinoma. Particularly, the pharmaceutical agent of the present invention exhibits remarkable inhibitory action on recurrence of hepatocellular carcinoma after treatment thereof, to thereby reduce recurrence rate of hepatocellular carcinoma, which has bad prognosis.

BRIEF DESCRIPTION OF THE DRAWING

FIG. 1 A graph showing the relationship between cumulative recurrence free rate and combined effect, wherein the horizontal axis denotes days passed from start of the test, and the vertical axis denotes cumulative recurrence free rate (%).

MODES FOR CARRYING OUT THE INVENTION

The definitions of terms used in the present specification are as follows. Unless otherwise specified, all the technical and science terms employed in the specification should have meanings generally understood by those skilled in the art to which the present invention pertains.

In one embodiment of the present invention, there is provided a pharmaceutical agent for the prevention and/or treatment of hepatocellular carcinoma, the agent containing an acyclic retinoid, a salt thereof, or a solvate of any of these, in combination with a branched-chain amino acid, a salt thereof, or a solvate of any of these (hereinafter, the pharmaceutical agent may be referred to as "the combined pharmaceutical agent of the present invention"). Namely, the combined pharmaceutical agent of the present invention is a pharmaceutical agent for the prevention and/or treatment of hepatocellular carcinoma, and the acyclic retinoid, a salt thereof, or a solvate of any of these, and the effective amount of a branched-chain amino acid, a salt thereof, or a solvate of any of these may be administered to a patient in need thereof simultaneously or separately at different points in time.

The class retinoid includes vitamin A (retionol) and homologous compounds thereof. These compounds are involved in morphogenesis, cell differentiation, cell proliferation control, etc. in the body. In terms of the structure thereof, retinoid is classified into cyclic retinoid and acyclic retinoid (retinoid/carotenoid, 14-20 (1997), published by Nanzan-Do). Examples of the cyclic retinoid include the aforementioned retionol, retinal, all-trans-retinoic acid (tretinoin), 9-cis-retinoic acid (alitretinoin), and 13-cis-retinoic acid (isotretinoin). In a broader sense, the class retinoid include synthetic compounds exhibiting bonding affinity to a retinoic acid receptor, even though the compounds have a chemical structure completely differing from that of vitamin A.

In the present invention, the term "acyclic retinoid" refers to, among the aforementioned broader-sense retinoids, a retinoid having no cyclic structure in the molecule thereof. Specific examples of the acyclic retinoid include geranylgeranoic acid, peretinoin, 2,3-dihydrogeranylgeranoic acid, 4,5-didehydro-10,11-dihydrogeranylgeranoic acid, 4,5,8,9-tetradehydrogeranylgeranoic acid, 4,5-didehydro-10,11,14,15-tetrahydrogeranylgeranoic acid, 14,15-dihydrogeranylgeranoic acid, methoprenic acid, hydroprenic acid, and phytanic acid. These acyclic retinoids may be used singly or in combination of two or more species. Notably, geranylgeranoic acid, which is a member of acyclic retinoid and is a component contained in medicinal plants, is known to increase the ceramide level of membrane lipid and to induce apoptosis of liver cancer cells, to thereby possibly serve as a cancer prophylactic and therapeutic agent (J. Lipid Res., 45 1092-1103 (2004)).

In the present invention, a salt of the acyclic retinoid may be also used. When the acyclic retinoid serves as a basic compound, examples of the salt include acid-added salts with an inorganic acid (e.g., hydrochloric acid, hydrobromic acid, hydroiodic acid, sulfuric acid, nitric acid, or phosphoric acid) or an organic acid (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid). When the acyclic retinoid serves as an acidic compound, examples of the salt include inorganic salts (e.g., sodium salts, potassium salts, lithium salts, barium salts, calcium salts, and magnesium salts) and organic salts (e.g., pyridinium salts, picolinium salts, and triethylammonium salts).

In the present invention, a solvate of the acyclic retinoid or a solvate of a salt of the acyclic retinoid may also be used. No particular limitation is imposed on the solvent which forms the solvate, and water or a physiologically acceptable organic solvent (e.g., ethanol, acetone, ethyl acetate, or hexane) may be used.

When several kinds of acyclic retinoids are used in combination, the retinoid salts or the solvates thereof may be identical to or different from one another.

The aforementioned acyclic retinoid, a salt thereof, and a solvate of any of these, in particular, the aforementioned compounds, are all known compounds and may be produced through a known method. For example, peretinoin may be produced through a method disclosed in JP-A-1981-140949. Alternatively, commercial acyclic retinoid products may also be used in the present invention.

In the present invention, the "acyclic retinoid, a salt thereof, or a solvate of any of these" is preferably peretinoin, a salt thereof, or a solvate of any of these, particularly preferably peretinoin.

In the present invention, examples of the "branched-chain amino acid" include α-amino acids having a branched carbon on the side chain of isoleucine, leucine, valine, and the like. In the present invention, these amino acids may be used singly or in combination of two or more species. Also, the branched-chain amino acid may be D-form, L-form, or a mixture thereof. In the present invention, L-form is preferred.

In the present invention, a salt of the branched-chain amino acid may be also used. When the branched-chain amino acid serves as a basic compound, examples of the salt include acid-added salts with an inorganic acid (e.g., hydrochloric acid, hydrobromic acid, hydroiodic acid, sulfuric acid, nitric acid, or phosphoric acid) or an organic acid (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, or glutamic acid). When the branched-chain amino acid serves as an acidic compound, examples of the salt include base-added salts such as inorganic salts (e.g., sodium salts, potassium salts, lithium salts, barium salts, calcium salts, and magnesium salts) and organic salts (e.g., pyridinium salts, picolinium salts, and triethylammonium salts).

In the present invention, a solvate of the branched-chain amino acid or a solvate of a salt of the branched-chain amino acid may also be used. No particular limitation is imposed on the solvent which forms the solvate, and water or a physiologically acceptable organic solvent (e.g., ethanol, acetone, ethyl acetate, or hexane) may be used.

When several kinds of branched-chain amino acids are used in combination, the branched-chain amino acid salts or the solvates thereof may be identical to or different from one another.

The aforementioned branched-chain amino acid, a salt thereof, and a solvate of any of these are known compounds and may be produced through a known method. Alternatively, commercial branched-chain amino acid products may also be used.

In the present invention, the "branched-chain amino acid, a salt thereof, or a solvate of any of these" is preferably a branched-chain amino acid containing at least one selected from the group consisting of isoleucine, leucine, and valine, a salt thereof, or a solvate of any of these, more preferably a branched-chain amino acid containing three amino acids: isoleucine, leucine, and valine, a salt thereof, or a solvate of any of these, particularly preferably a branched-chain amino acid composed of three amino acids: isoleucine, leucine, and valine. When the branched-chain amino acid, a salt thereof, or a solvate of any of these contains isoleucine, leucine, and valine, no particular limitation is imposed on the compositional proportions among the three components. Preferably, the proportions by mass of isoleucine (free form): leucine (free form): valine (free form) are 1:0.5 to 3:0.4 to 2, more preferably 1:1 to 2:0.8 to 1.4.

In one preferred embodiment of the present invention, the "branched-chain amino acid, a salt thereof, or a solvate of any of these" has compositional proportions by mass among three branched-chain amino acids (i.e., isoleucine, leucine, and valine) of isoleucine (free form) 952 parts by mass:leucine (free form) 1,904 parts by mass:valine (free form) 1,144 parts by mass. A single composition containing isoleucine (free form), leucine (free form), and valine (free form) at the above proportions by mass is particularly preferred. The composition may be produced through a known method as a peroral preparation or a parenteral preparation.

Particularly preferably, the composition contains isoleucine (952 mg), leucine (1,904 mg), and valine (1,144 mg). Preferably, the composition is administered trice a day. Although the composition may be produced through a known method, a commercial product of the composition (e.g., isoleucine (952 mg), leucine (1,904 mg), and valine (1,144 mg) in one package) may be used. Examples of the commercial product include Aminovact (registered trademark) combination granules (product of Nichi-Iko Pharmaceutical Co., Ltd.), Aminomylan combination granules (product of Mylan Seiyaku), Coveneal (registered trademark) combination granules (product of Yoshindo Inc.), Branute (registered trademark) granules (product of Nihon Pharmaceutical Co., Ltd.), Hepaact (registered trademark) combination granules (product of To a Pharmaceuticals Co., Ltd.), Lickle (registered trademark) combination granules (product of Sawai Pharmaceutical Co., Ltd.), Livact (registered trademark) combination granules (product of Ajinomoto Pharmaceuticals Co., Ltd.), Liverevan (registered trademark) combination granules (product of Medisa Shinyaku Inc.), and Leovacton (registered trademark) combination granules (divided) (product of Choseido Pharmaceutical Co., Ltd.). Any of the above commercial products is preferably administered, thrice a day, one package as a single dose.

In the present invention, no particular limitation is imposed on the ratio of amount of acyclic retinoid, a salt thereof, or a solvate of any of these, to amount of branched-chain amino acid, a salt thereof, or a solvate of any of these, and the ratio may be appropriately adjusted so that effects of interest on the prevention and/or treatment of hepatocellular carcinoma can be attained. In the case where the acyclic retinoid is peretinoin, and the branched-chain amino acid contains isoleucine, leucine, and valine, a salt thereof, or a solvate of any of these, the total amount of isoleucine (free form), leucine (free form), and valine (free form) is preferably 1 to 5,000 parts by mass, with respect to 1 part by mass of peretinoin (free form), more preferably 5 to 200 parts by mass, particularly preferably 10 to 100 parts by mass.

In the present invention, the expression "the prevention and/or treatment of hepatocellular carcinoma" refers to a concept encompassing prevention of the onset of hepatocellular carcinoma, inhibition of progress of hepatocellular carcinoma, treatment of hepatocellular carcinoma, and inhibition of recurrence of hepatocellular carcinoma after treatment thereof. The pharmaceutical agent of the present invention may be suitably used as a pharmaceutical agent for inhibition of recurrence of hepatocellular carcinoma after treatment thereof, particularly for inhibition of recurrence of hepatocellular carcinoma after radical treatment thereof. In the "inhibition of recurrence of hepatocellular carcinoma after treatment thereof," examples of the hepatocellular carcinoma therapeutic method include surgical therapies such as hepatectomy, total liver transplantation, and partial liver transplantation; percutaneous local therapies such as percutaneous ethanol injection therapy (PEIT), percutaneous microwave coagulation therapy (PMCT), and radiofrequency ablation (RFA); transcatheter arterial infusion (TAI); transcatheter arterial embolization (TAE), in which artery embolization is performed with an embolizaton substance such as gelatin sponge, porous gelatin granules, Embosephere (trisacrylic-gelatin spherical particles), superabsorbent polymer microspheres (SAP-MS), HepaSphere, Embozene (special fluoro-coating-treated acrylic hydrogel), or polyvinyl alcohol; transcatheter arterial chemoembolization (TACE), in which embolization is performed by using an anti-cancer agent such as epirubicin hydrochloride, cisplatin, doxorubicin hydrochloride, or mytomycin C, and by using the aforementioned embolization substance after lipiodolization, or by using drug (anti-cancer agent)-eluting beads (DEB); and pharmacotherapy employing glycyrrhizic acid, shosaikoto, interferon, peginterferon, ribavirin, 5-fluorouracil, cisplatin, oxaliplatin, doxorubicin hydrochloride, epirubicin hydrochloride, mitoxantrone hydrochloride, etoposide, irinotecan hydrochloride, gemcitabine hydrochloride, docetaxel hydrate, sorafenib tosylate, erlotinib hydrochloride, pitavastatin calcium, etc.

The pharmaceutical agent of the present invention may be administered before and after the prevention/treatment of hepatocellular carcinoma or during the course thereof. No particular limitation is imposed on the hepatocellular carcinoma therapeutic method, and the aforementioned methods may be employed. Two or more of the methods may be combined. In the present invention, surgical therapy and local medical treatment are preferred.

In the present invention, no particular limitation is imposed on the cause of hepatocellular carcinoma, and examples of the cause include chronic hepatitis and cirrhosis (viral, alcoholic, fatty liver, non-alcoholic). The present invention may be suitably applied to a hepatocellular carcinoma caused by hepatitis virus or non-alcoholic steatohepatitis, more suitably a hepatocellular carcinoma caused by hepatitis virus (preferably hepatitis virus-positive hepatocellular carcinoma), even more suitably a hepatocellular carcinoma caused by at least one virus selected from the group consisting of hepatitis B virus and hepatitis C virus (preferably a hepatocellular carcinoma positive to at least one virus selected from the group consisting of hepatitis B virus and hepatitis C virus), particularly suitably a hepatocellular carcinoma caused by hepatitis C virus (preferably a hepatitis C virus-positive hepatocellular carcinoma). As specifically disclosed in the Example, the pharmaceutical agent of the present invention exhibited excellent recurrence inhibitory effect with respect to patients after treatment of a hepatocellular carcinoma caused by a hepatitis virus such as hepatitis C virus, to thereby improve prognosis. Therefore, the pharmaceutical agent of the present invention may be particularly suitably used for inhibition of recurrence of a hepatocellular carcinoma caused by a hepatitis virus such as hepatitis C virus, after the treatment thereof.

In addition, since the pharmaceutical agent of the present invention can inhibit recurrence of hepatocellular carcinoma after the treatment thereof, further invasion can be avoided in the treatment of recurred hepatocellular carcinoma. Thus, the pharmaceutical agent of the present invention may be suitably used as a pharmaceutical agent for inhibition of recurrence of hepatocellular carcinoma after the treatment thereof.

The pharmaceutical agent of the present invention may further contain, in addition to the acyclic retinoid, a salt thereof, or a solvate of any of these, and the branched-chain amino acid, a salt thereof, or a solvate of any of these, a "non-branched-chain amino acid, a salt thereof, or a solvate of any of these." The thus-combined ingredients may be administered.

In the present invention, examples of the "non-branched-chain amino acid" include amino acids other than the aforementioned "branched-chain amino acid," such as glycine, alanine, serine, threonine, aspartic acid, glutamic acid, lysine, arginine, cysteine, cystine, methionine, phenylalanine, tyrosine, tryptophan, histidine, and proline. These amino acids may be used singly or in combination of two or more species. Among them, glycine, alanine, serine, threonine, lysine, arginine, methionine, phenylalanine, tryptophan, histidine, and proline are preferred as non-branched-chain amino acids employed in the present invention. The non-branched-chain amino acid may be D-form, L-form, or a mixture thereof, and among these, the L-form is preferred.

In the present invention, a salt of the non-branched-chain amino acid may be used. The same type of the salts as mentioned in relation to the branched-chain amino acid may also be used. Also, a solvate of the non-branched-chain amino acid or a solvate of the salt of the non-branched-chain amino acid may be used. The same type of the solvates as mentioned in relation to the branched-chain amino acid may also be used.

When several kinds of non-branched-chain amino acids are used in combination, the salts or solvates of the non-branched-chain amino acid may be identical to or different from one another. The non-branched-chain amino acid, a salt thereof, and a solvate of any of these are known compounds and may be produced through a known method. Alternatively, commercial non-branched-chain amino acid products may also be used.

In the present invention, in the case where the non-branched-chain amino acid, a salt thereof, or a solvate of any of these is administered with essential ingredients, there may be employed a composition at least containing a branched-chain amino acid, a salt thereof, or a solvate of any of these, and a non-branched-chain amino acid, a salt thereof, or a solvate of any of these.

Specific examples of such compositions include the following (i) to (iii).

(i) A composition containing isoleucine (0.9 parts by mass), leucine (1.1 parts by mass), and valine (0.84 parts by mass); and threonine (0.45 parts by mass), serine (0.5 parts by mass), proline (0.8 parts by mass), cysteine hydrochloride hydrate (0.04 parts by mass, 0.03 parts by mass as cysteine), glycine (0.9 parts by mass), alanine (0.75 parts by mass), methionine (0.1 parts by mass), phenylalanine (0.1 parts by mass), tryptophan (0.07 parts by mass), lysine hydrochloride (0.76 parts by mass, 0.61 parts by mass as lysine), histidine hydrochloride (0.32 parts by mass, 0.24 parts by mass as histidine), and arginine hydrochloride (0.73 parts by mass, 0.6 parts by mass as arginine).

The composition may be produced through a known method as a peroral preparation or a parenteral preparation. A commercial product of the composition may also be used.

Another preferred embodiment of the present invention is a parenteral composition (parenteral preparation) containing isoleucine (0.9 w/v %), leucine (1.1 w/v %), and valine (0.84 w/v %), and non-branched-chain amino acids: threonine (0.45 w/v %, serine (0.5 w/v %), proline (0.8 w/v %), cysteine hydrochloride hydrate (0.04 w/v %, 0.03 w/v % as cysteine), glycine (0.9 w/v %), alanine (0.75 w/v %), methionine (0.1 w/v %), phenylalanine (0.1 w/v %), tryptophan (0.07 w/v %), lysine hydrochloride (0.76 w/v %, 0.61 w/v % as lysine), histidine hydrochloride (0.32 w/v %, 0.24 w/v % as histidine), and arginine hydrochloride (0.73 w/v %, 0.6 w/v % as arginine). There may also be employed commercial injection products of the composition such as Aminoleban (registered trademark) intravenous drip (product of Otsuka Pharmaceutical Factory, Inc.), Terufis (registered trademark) intravenous drip (product of Terumo Corporation), Hikarilevan (registered trademark) injection (product of Hikari Pharmaceutical Co., Ltd.), and Morihepamin (registered trademark) (product of Ajinomoto Pharmaceuticals Co., Ltd.) intravenous drip. The aforementioned Aminoleban intravenous drip is preferably administered at a single dose of 500 to 1000 mL. Terufis intravenous drip is preferably administered at a single dose of 500 to 1000 mL. Hikarilevan intravenous drip is preferably administered at a single dose of 500 to 1000 mL. Morihepamin intravenous drip is preferably administered at a single dose of 500 mL.

(ii) A composition containing isoleucine (1.9225 parts by mass), leucine (2.037 parts by mass), and valine (1.602 parts by mass); and lysine hydrochloride (0.2425 parts by mass), threonine (0.133 parts by mass), arginine hydrochloride (0.302 parts by mass), histidine hydrochloride (0.1875 parts by mass), and tryptophan (0.0735 parts by mass).

The composition may be produced through a known method as a peroral preparation or a parenteral preparation. There may be also employed a commercial product of the composition such as Aminoleban (registered trademark) EN combination powder (product of Otsuka Pharmaceutical Co., Ltd.), whose one package (50 g) contains isoleucine (1.9225 g), leucine (2.037 g), and valine (1.602 g); and lysine hydrochloride (0.2425 g), threonine (0.133 g), arginine hydrochloride (0.302 g), histidine hydrochloride (0.1875 g), and tryptophan (0.0735 g). Aminoleban EN combination powder is preferably administered thrice a day at a single dose of one package.

(iii) A BCAA-free composition containing isoleucine (1,730 parts by mass), leucine (2,122 parts by mass), and valine (1,615 parts by mass); and lysine hydrochloride (974 parts by mass), methionine (117 parts by mass), phenylalanine (117 parts by mass), threonine (436 parts by mass), tryptophan (56 parts by mass), histidine (306 parts by mass), arginine (1,647 parts by mass), arginine hydrochloride (108 parts by mass), alanine (978 parts by mass), glycine (430 parts by mass), proline (522 parts by mass), and serine (257 parts by mass).

The composition may be produced through a known method as a peroral preparation or a parenteral preparation. There may be also employed a commercial product of the composition such as Hepan ED (registered trademark) combined integral drug (product of Ajinomoto Pharmaceuticals Co., Ltd.), whose one package (80 g) contains isoleucine (1,730 mg), leucine (2,122 mg), and valine (1,615 mg); and lysine hydrochloride (974 mg), methionine (117 mg), phenylalanine (117 mg), threonine (436 mg), tryptophan (56 mg), histidine (306 mg), arginine (1,647 mg), arginine hydrochloride (108 mg), alanine (978 mg), glycine (430 mg), proline (522 mg), and serine (257 mg). Hepan ED combination internal drug is preferably administered twice a day at a single dose of one package.

Further non-limitative examples of the composition containing branched amino acids include Aminosyn (product of HOSPIRA), Branchamin (product of BAXTER HEALTHCARE), Hepatasol (product of BAXTER HEALTHCARE), Novamine (product of HOSPIRA), Prosol (product of BAXTER HEALTHCARE), and Travasol (product of BAXTER HEALTHCARE).

No particular limitation is imposed on the form of the combined pharmaceutical agent of the present invention, and specific examples of the form include the following (I) and (II):

(I) a form of a single preparation (combination drug) containing an acyclic retinoid, a salt thereof, or a solvate of any of these, in combination with a branched-chain amino acid, a salt thereof, or a solvate of any of these, and (II) a form for separately administering a preparation containing an acyclic retinoid, a salt thereof, or a solvate of any of these, and a preparation containing a branched-chain amino acid, a salt thereof, or a solvate of any of these.

In the case of form (II), the preparations may be administered to a patient in need thereof simultaneously or separately at different points in time with an appropriate interval, and an appropriate dosing regimen may be employed so that an effect of interest on the prevention and/or treatment of hepatocellular carcinoma can be attained. The form for separately administering a preparation containing an acyclic retinoid, a salt thereof, or a solvate of any of these, and a preparation containing a branched-chain amino acid, a salt thereof, or a solvate of any of these may be provided as a kit preparation including two preparations in combination in a single package.

No particular limitation is imposed on the administration route of the pharmaceutical agent of the present invention, either peroral administration or parenteral administration may be employed. In the case of the aforementioned form (II), one preparation may be a peroral preparation, and the other may be a parenteral preparation. Examples of the peroral preparation include tablet, capsule, granule, powder, and syrup, and examples of the parenteral preparation include injection, suppository, inhalation, percutaneous absorption drug, skin external drug, eye drop, and nose drop. Among these administration forms, peroral preparations are preferred, with tablet, capsule, granule, powder, syrup, etc. being particularly preferred.

Such peroral preparations and parenteral preparations may be produced with known additives for drug preparation through a known method disclosed in, for example, "The Japanese Pharmacopoeia 15th Edition, General Rules for Preparations."

No particular limitation is imposed on the dose of the pharmaceutical agent of the present invention, and the dose may be appropriately adjusted depending on various conditions such as the age, body weight, and symptom of the patient, administration form, and administration frequency. In the case where the acyclic retinoid is peretinoin, and the branched-chain amino acid includes isoleucine, leucine, and valine in combination, the daily dose of peretinoin (free form) for an adult is 10 mg to 10 g, preferably 100 mg to 5 g, more preferably 300 mg to 1 g, particularly preferably 500 mg to 900 mg. Similarly, the daily dose of branched-chain amino acid, as the total amount of isoleucine (free form), leucine (free form), and valine (free form), is 1 g to 50 g, preferably 5 g to 35 g, more preferably 10 g to 30 g. In administration, the dose may be a daily dose or divided into a plurality of portions.

In another embodiment of the present invention, there is provided a pharmaceutical agent containing an acyclic retinoid, a salt thereof, or a solvate of any of these, to be administered in combination with a branched-chain amino acid, a salt thereof, or a solvate of any of these, for the prevention and/or treatment of hepatocellular carcinoma. The pharmaceutical agent of this embodiment contains, as an ingredient, an acyclic retinoid, a salt thereof, or a solvate of any of these, and is administered with a branched-chain amino acid, a salt thereof, or a solvate of any of these, to a patient in need thereof simultaneously or separately at different points in time, for the prevention and/or treatment of hepatocellular carcinoma.

A specific example of the pharmaceutical agent of this embodiment is a kit for the prevention and/or treatment of hepatocellular carcinoma, the kit containing the following (1) and (2):

(1) a pharmaceutical agent for the prevention and/or treatment of hepatocellular carcinoma, the agent containing an acyclic retinoid, a salt thereof, or a solvate of any of these; and (2) a direction which directs the pharmaceutical agent to be administered in combination with a branched-chain amino acid, a salt thereof, or a solvate of any of these. Specific examples of the direction include a so-called specification (package insert) describing effect, efficacy, direction for use, dose, etc.

In this embodiment, the meanings of the terms, amounts of the ingredients, drug preparation processes, etc. are the same as described above.

In further embodiment of the present invention, there is provided a pharmaceutical agent containing a branched-chain amino acid, a salt thereof, or a solvate of any of these, to be administered in combination with an acyclic retinoid, a salt thereof, or a solvate of any of these, for the prevention and/or treatment of hepatocellular carcinoma. The pharmaceutical agent of this embodiment contains, as an ingredient, a branched-chain amino acid, a salt thereof, or a solvate of any of these, and is administered with an acyclic retinoid, a salt thereof, or a solvate of any of these, to a patient in need thereof, simultaneously or separately at different points in time, for the prevention and/or treatment of hepatocellular carcinoma. A specific example of the pharmaceutical agent of this embodiment is a kit for the prevention and/or treatment of hepatocellular carcinoma, the kit containing the following (1) and (2):

(1) a pharmaceutical agent for the prevention and/or treatment of hepatocellular carcinoma, the agent containing a branched-chain amino acid, a salt thereof, or a solvate of any of these; and (2) a direction which directs the pharmaceutical agent to be administered in combination with an acyclic retinoid, a salt thereof, or a solvate of any of these. Specific examples of the direction include a so-called specification (package insert) describing effect, efficacy, direction for use, dose, etc.

The meanings of the terms, amounts of the ingredients, drug preparation processes, etc. are the same as described above.

EXAMPLES

The present invention will next be described in more detail, by way of examples, which should not be construed as limiting the invention thereto.

Example 1

Drugs Employed

Peretinoin produced through a known method was used as an acyclic retinoid. A commercial preparation containing isoleucine, leucine, and valine in combination was used as a branched-chain amino acid.

[Procedure]

Forty-six subjects (age: 49 to 80) were tested. The subjects were HCV-positive, underwent radical treatment (surgical therapy or local medical therapy) of primary occurrence or first recurrence of hepatocellular carcinoma, had a Child-Pugh grade of A or B, and had no statistical significance in the cause before administration. As a preparation containing a branched-chain amino acid, Aminoleban (registered trademark) EN combination powder or Livact (registered trademark) combination granules were administered in a specific amount during the test period. The daily dose of Aminoleban was 150 g (the daily dose including L-isoleucine (5.7675 g), L-leucine (6.111 g), and L-valine (4.806 g)), and that of Livact was 12.45 g (the daily dose including L-isoleucine (2.856 g), L-leucine (5.712 g), and L-valine (3.432 g)). As an acyclic retinoid, peretinoin, was administered to the subjects in combination with the branched-chain amino acid. The subjects were divided into the following groups:

1: peretinoin 600 mg (daily dose, the same applies hereinafter) combination group: 18 subjects (male: 11, female: 7), 2: peretinoin 300 mg combination group: 15 subjects (male: 9, female: 6), and 3: branched-chain amino acid sole administration group: 13 subjects (male: 8, female: 5).

The daily dose of peretinoin was divided into two portions. On each day during 96 weeks after start of the test, peretinoin was perorally administered after meal.

Radical curing and recurrence of hepatocellular carcinoma were confirmed through dynamic CT measured every 12 weeks after the start of the test. The combinatory effect on cumulative recurrence free rate was evaluated through the log-rank test.

FIG. 1 shows the results. Also, Table 1 shows the data of 50% recurrence free interval (i.e., the interval until hepatocellular carcinoma recurrence was observed in 50% of the subjects) and 75% recurrence free interval (i.e., the interval until hepatocellular carcinoma recurrence was observed in 25% of the subjects).

TABLE 1

| | Groups | 50% Recurrence free interval (days) | 75% Recurrence free interval (days) |
|---|---|---|---|
| 1 | Combination with 600 mg peretinoin | >730 | 705 |
| 2 | Combination with 300 mg peretinoin | >730 | 415 |
| 3 | Sole branched amino acids | 343 | 188 |

As is clear from FIG. 1, remarkable improvement in terms of cumulative recurrence free rate was observed in the peretinoin 600 mg combination group and the peretinoin 300 mg combination group. Particularly, the cumulative recurrence free rate of the 600 mg combination group was significantly improved, as compared with the sole branched-chain amino acid administration group (P=0.020, Log-rank test).

As is clear from Table 1, the 75% recurrence free interval was found to extend for 517 days (600 mg administration group) and for 227 days (300 mg administration group), as compared with the sole branched-chain amino acid administration group. In the peretinoin and branched-chain amino acid combination groups, the 50% recurrence free interval was found to extend more than double, as compared with the sole branched-chain amino acid administration group.

Therefore, administration of peretinoin in combination with branched-chain amino acid was found to reduce the hepatocellular carcinoma recurrence rate. Particularly when peretinoin (600 mg) and a branched-chain amino acid were administered in combination, the cumulative recurrence free rate was found to be significantly improved, as compared with the case of sole administration of a branched-chain amino acid.

The above study results have revealed that use of an acyclic retinoid in combination with a branched-chain amino acid results in a remarkably excellent effect of inhibiting recurrence of hepatocellular carcinoma after treatment thereof. Thus, the combination of an acyclic retinoid and a branched-chain amino acid has been proven to serve as a useful pharmaceutical agent for the prevention and/or treatment of hepatocellular carcinoma.

INDUSTRIAL APPLICABILITY

The pharmaceutical agent of the present invention may be used as a pharmaceutical agent for the prevention and/or treatment of hepatocellular carcinoma. Thus, the present invention has industrial applicability.

The invention claimed is:

1. A pharmaceutical agent that comprises peretinoin, optionally in free form, and a combination of branched chain amino acids that comprises isoleucine, leucine, and valine, each of isoleucine, leucine, and valine is optionally in free form, in amounts effective to inhibit recurrence of hepatocellular carcinoma in a subject after the treatment thereof.

2. The agent of claim 1, wherein the isoleucine, leucine, and valine are present in proportions of 1:0.5 to 3:0.4 to 2 relative to each other.

3. A kit comprising the agent of claim 2 and directions for administration of the agent to a subject.

4. The agent of claim 1, wherein the isoleucine, leucine, and valine are present in proportions 1:1 to 2:0.8 to 1.4 relative to each other.

5. A kit comprising the agent of claim 4 and directions for administration of the agent to a subject.

6. The agent of claim 1, wherein the total amount of isoleucine, which is in free form, leucine, which is in free form, and valine, which is in free form is from 1 to 5,000 parts by mass, with respect to 1 part by mass of peretinoin, which is in free form.

7. A kit comprising the agent of claim 6 and directions for administration of the agent to a subject.

8. The agent of claim 1, wherein the total amount of isoleucine, which is in free form, leucine, which is in free form, and valine, which is in free form is from 5 to 200 parts by mass with respect to 1 part by mass of peretinoin, which is in free form.

9. A kit comprising the agent of claim 8 and directions for administration of the agent to a subject.

10. The agent of claim 1, wherein the total amount of isoleucine, which is in free form, leucine, which is in free form, and valine, which is in free form is from 10 to 100 parts by mass with respect to 1 part by mass of peretinoin, which is in free form.

11. A kit comprising the agent of claim 10 and directions for administration of the agent to a subject.

12. The agent of claim 1, comprising peretinoin in an amount of 10 mg to 10 g and the combination of branched-chain amino acids in an amount of 1 g to 50 g.

13. A kit comprising the agent of claim 12 and directions for administration of the agent to a subject.

14. The agent of claim 1, comprising peretinoin in an amount of 500 mg to 900 mg and the combination of branched-chain amino acids in an amount of 10 g to 30 g.

15. A kit comprising the agent of claim 14 and directions for administration of the agent to a subject.

16. A kit comprising the agent of claim 1 and directions for administration of the agent to a subject.

17. The agent of claim 1, comprising a single daily dose of peretinoin and a single daily dose of the combination of branched chain amino acids.

18. The agent of claim 1, comprising a plurality of daily dosages of peretinoin and a plurality of daily dosages of the combination of branched chain amino acids.

19. The agent of claim 1, comprising a single daily dose of either peretinoin or the combination of branched chain amino acids and a plurality of daily dosages for the other of peretinoin or the combination of branched chain amino acids.

20. A method of inhibiting recurrence of hepatocellular carcinoma in a subject in need thereof, the method comprising administering to the subject effective amounts of peretinoin, optionally in free form, and a combination of branched chain amino acids that comprises isoleucine, leucine, and valine, each of isoleucine, leucine, and valine is optionally in free form, to inhibit recurrence of hepatocellular carcinoma in a subject the treatment thereof.

21. The method of claim 20, wherein the isoleucine, leucine, and valine are present in proportions of 1:0.5 to 3:0.4 to 2 relative to each other.

22. The method of claim 20, wherein the isoleucine, leucine, and valine are present in proportions 1:1 to 2:0.8 to 1.4 relative to each other.

23. The method of claim 20, wherein the total amount of isoleucine, which is in free form, leucine, which is in free form, and valine, which is in free form is from 1 to 5,000 parts by mass, with respect to 1 part by mass of peretinoin, which is in free form.

24. The method of claim 20, wherein the total amount of isoleucine, which is in free form, leucine, which is in free form, and valine, which is in free form is from 5 to 200 parts by mass with respect to 1 part by mass of peretinoin, which is in free form.

25. The method of claim 20, wherein the total amount of isoleucine, which is in free form, leucine, which is in free form, and valine, which is in free form is from 10 to 100 parts by mass with respect to 1 part by mass of peretinoin, which is in free form.

26. The method of claim 20, comprising administering peretinoin in an amount of 10 mg to 10 g and the combination of branched-chain amino acids in an amount of 1 g to 50 g.

27. The method of claim 20, comprising administering peretinoin in an amount of preferably 500 mg to 900 mg and the combination of branched-chain amino acids in an amount of 10 g to 30 g.

28. The method of claim 20, comprising administering a single daily dose of peretinoin and a single daily dose of the combination of branched chain amino acids.

29. The method of claim 20, comprising administering a plurality of daily dosages of peretinoin and a plurality of daily dosages of the combination of branched chain amino acids.

30. The method of claim 20, comprising administering a single daily dose of either peretinoin or the combination of branched chain amino acids and a plurality of daily dosages for the other of peretinoin or the combination of branched chain amino acids.

* * * * *